(12) United States Patent
Fu et al.

(10) Patent No.: US 10,583,193 B2
(45) Date of Patent: Mar. 10, 2020

(54) CELL PENETRATING PEPTIDE INHIBITORS OF P53-MDM2 INTERACTION

(71) Applicant: Sorrento Therapeutics, Inc., San Diego, CA (US)

(72) Inventors: Yanwen Fu, San Diego, CA (US); Gunnar F. Kaufmann, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/880,101

(22) Filed: Jan. 25, 2018

(65) Prior Publication Data

US 2018/0207285 A1 Jul. 26, 2018

Related U.S. Application Data

(60) Provisional application No. 62/489,494, filed on Apr. 25, 2017, provisional application No. 62/450,297, filed on Jan. 25, 2017.

(51) Int. Cl.
*A61K 47/54* (2017.01)
*C07K 19/00* (2006.01)
(Continued)

(52) U.S. Cl.
CPC ............ *A61K 47/549* (2017.08); *A61K 38/10* (2013.01); *A61K 47/64* (2017.08); *A61P 35/00* (2018.01);
(Continued)

(58) Field of Classification Search
CPC ...... A61K 38/10; A61K 47/549; A61K 47/64; A61P 35/00; C07K 19/00; C07K 9/00; C07K 9/003
See application file for complete search history.

(56) References Cited

U.S. PATENT DOCUMENTS

2005/0227932 A1 10/2005 Lu et al.
2015/0353606 A1 12/2015 Skerlj et al.

FOREIGN PATENT DOCUMENTS

WO 2003041715 A1 5/2003

OTHER PUBLICATIONS

Morrison et al. (Chem. Commun., vol. 51:13470-13473 (2015) (Year: 2015).*

(Continued)

*Primary Examiner* — Randall L Beane
(74) *Attorney, Agent, or Firm* — McNeill Baur PLLC

(57) ABSTRACT

Provided are compounds having the Formula I or II:

(I)

(Continued)

-continued

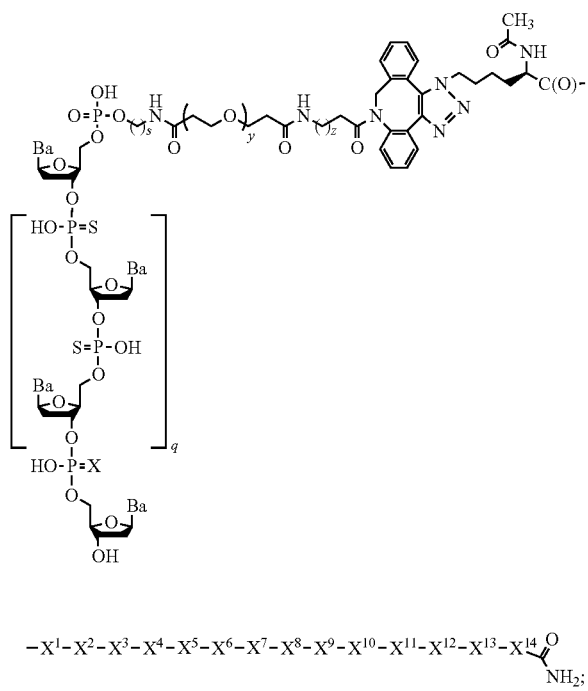

(51) Int. Cl.
 A61P 35/00 (2006.01)
 A61K 38/10 (2006.01)
 C07K 9/00 (2006.01)
 A61K 47/64 (2017.01)
(52) U.S. Cl.
 CPC ............... *C07K 9/00* (2013.01); *C07K 9/003* (2013.01); *C07K 19/00* (2013.01)

(56) References Cited

OTHER PUBLICATIONS

PubChem Open Chemistry Database, US National Library of Medicine, "Compound Summary for CID 89409686," modified on May 8, 2018, created on Feb. 13, 2015.
PubChem Open Chemistry Database, US National Library of Medicine, "Compound Summary for CID 101905670," modified on May 8, 2018, created on Dec. 18, 2015.
International Search Report relating to corresponding international application No. PCT/IB18/50466, completed May 9, 2018, dated May 23, 2018.

* cited by examiner and pharmaceutically acceptable salts thereof, pharmaceutical compositions thereof, and their use in the treatment of cancers.

12 Claims, 4 Drawing Sheets

Specification includes a Sequence Listing.

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleoside

<400> SEQUENCE: 1
tccatgagct tcctgatgct                                              20

<210> SEQ ID NO 2
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
```

```
<222> LOCATION: (15)..(15)
<223> OTHER INFORMATION: azidolysine
<220> FEATURE:
<221> NAME/KEY: MOD_RES
<222> LOCATION: (15)..(15)
<223> OTHER INFORMATION: AMIDATION

<400> SEQUENCE: 2

Leu Thr Phe Xaa Glu Tyr Trp Xaa Gln Leu Xaa Ser Ala Ala Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: azidolysine
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (9)..(9)
<223> OTHER INFORMATION: Aib
<220> FEATURE:
<221> NAME/KEY: MOD_RES
<222> LOCATION: (12)..(12)
<223> OTHER INFORMATION: Aib
<220> FEATURE:
<221> NAME/KEY: MOD_RES
<222> LOCATION: (15)..(15)
<223> OTHER INFORMATION: AMIDATION

<400> SEQUENCE: 3

Lys Leu Thr Phe Xaa Glu Tyr Trp Xaa Gln Leu Xaa Ser Ala Ala
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetically modified natural sequence of p53
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: azidolysine
<220> FEATURE:
<221> NAME/KEY: MOD_RES
<222> LOCATION: (14)..(14)
<223> OTHER INFORMATION: AMIDATION

<400> SEQUENCE: 4

Leu Thr Phe Glu His Tyr Trp Ala Gln Leu Thr Ser Ala Lys
1               5                   10
```

CELL PENETRATING PEPTIDE INHIBITORS OF P53-MDM2 INTERACTION

RELATED APPLICATIONS

This application claims priority to U.S. Provisional Application No. 62/450,297, filed on Jan. 25, 2017, and U.S. Provisional Application No. 62/489,494, filed on Apr. 25, 2017. The entire contents of each of the foregoing applications are hereby incorporated herein by reference.

SEQUENCE LISTING

The instant application contains a Sequence Listing which has been submitted herewith in a file with ASCII format. Said file with ASCII format, created on Jan. 25, 2018, is named S103014 1850W0 ST25.txt and is 2110 bytes in size.

BACKGROUND

Approximately 27 million people are living with a tumor in which the tumor suppressing activity of p53 has been inactivated. See e.g., Trends in Pharmacological Sciences, January 2011, Vol. 32, No. 1. The primary response to certain cell stresses is activation of p53 within the cell. Murine double minute 2 (MDM2) is an E3 ubiquitin ligase that targets p53 for ubiquitin-dependent degradation, and ensures that p53 is regulated by limiting p53 growth in unstressed cells. Disruption of the MDM2-p53 interaction leads to p53 induction and subsequent prevention of tumor formation. The generation of small molecules inhibitors of the MDM2-p53 interaction have therefore been of great interest.

One particular class of small molecules that have been of recent interest are peptide inhibitors. See e.g., PNAS, Sep. 3, 2013, Vol. 110, No. 36, E3445-E3454; Molecular Cancer Research, Vol. 1, 1001-1008, December 2003; and Trends in Pharmacological Sciences, January 2011, Vol. 32, No. 1. Although peptide scaffolds have been an integral design in potential drug candidates, peptides are typically restricted by their limited access to intracellular compartments, i.e., poor permeability. Additionally, even in instances where intracellular admission is achieved, peptides may be partially degraded, leading to incomplete presentation for target recognition.

The need therefore exists for p53-MDM2 inhibitors which have high cellular uptake and which are presented inside cells where disease-causing proteins are located.

SUMMARY

It has now been found that the compounds described herein, and pharmaceutically acceptable compositions thereof, effectively inhibit the p53-MDM2 interaction. See e.g., FIG. 1. Such compounds include those having the Formula I or II:

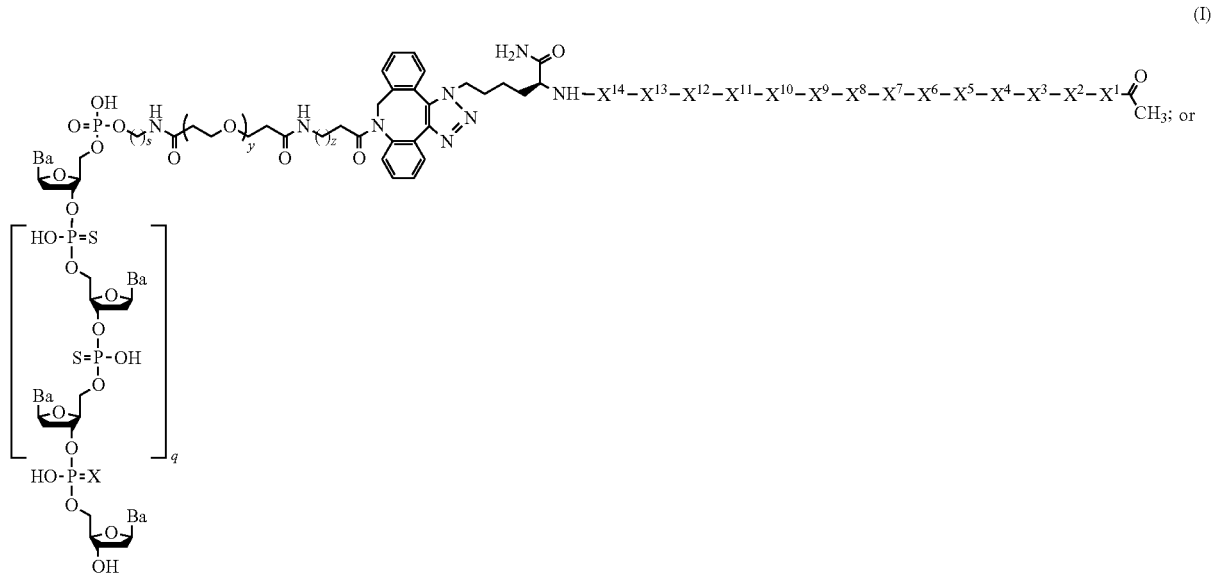

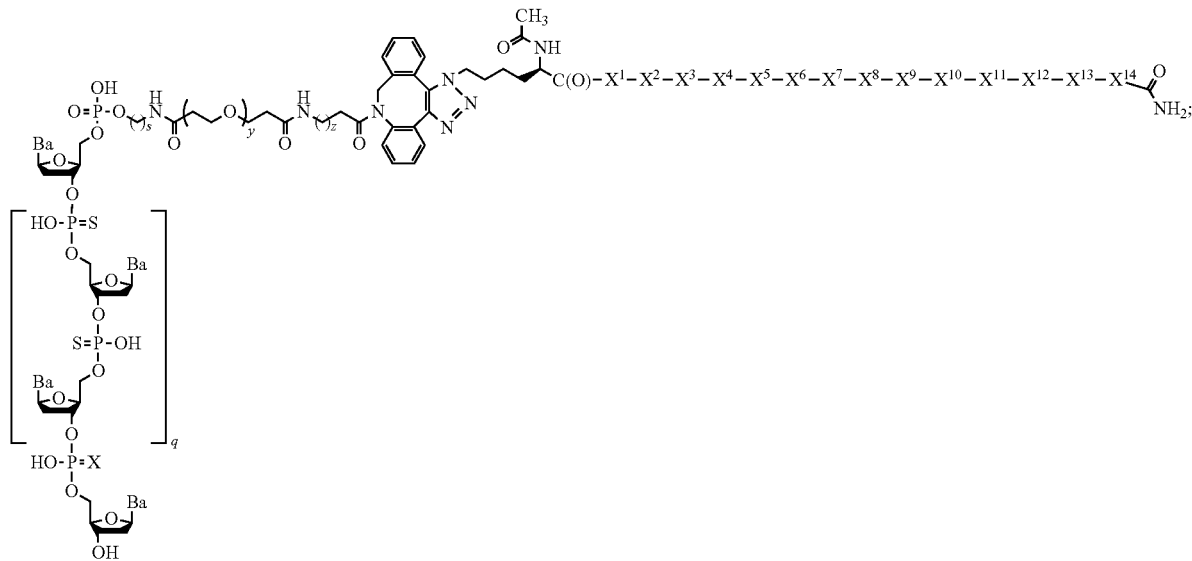

(II)

or a pharmaceutically acceptable salt thereof, wherein each of Ba, X, q, s, y, z, and $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$ are as defined herein.

Also provided are methods of using the disclosed compounds in the treatment of one of more cancers described herein.

DETAILED DESCRIPTION

1. General Description of Compounds

Figure 1:
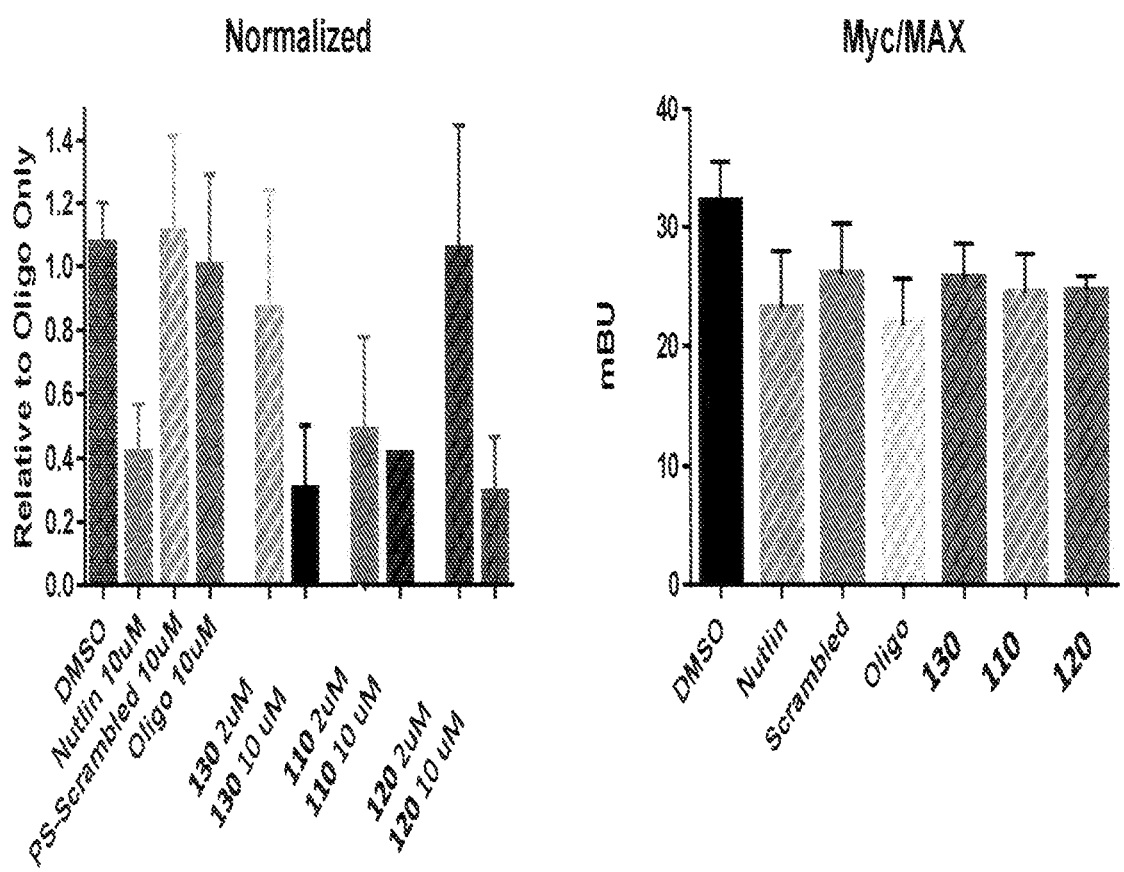
FIG. 1 shows the results from a p53-MDM2 inhibition assay using compounds 110 120, and 130 as described herein.

In certain embodiments, the present disclosure provides a compound of Formula I or II:

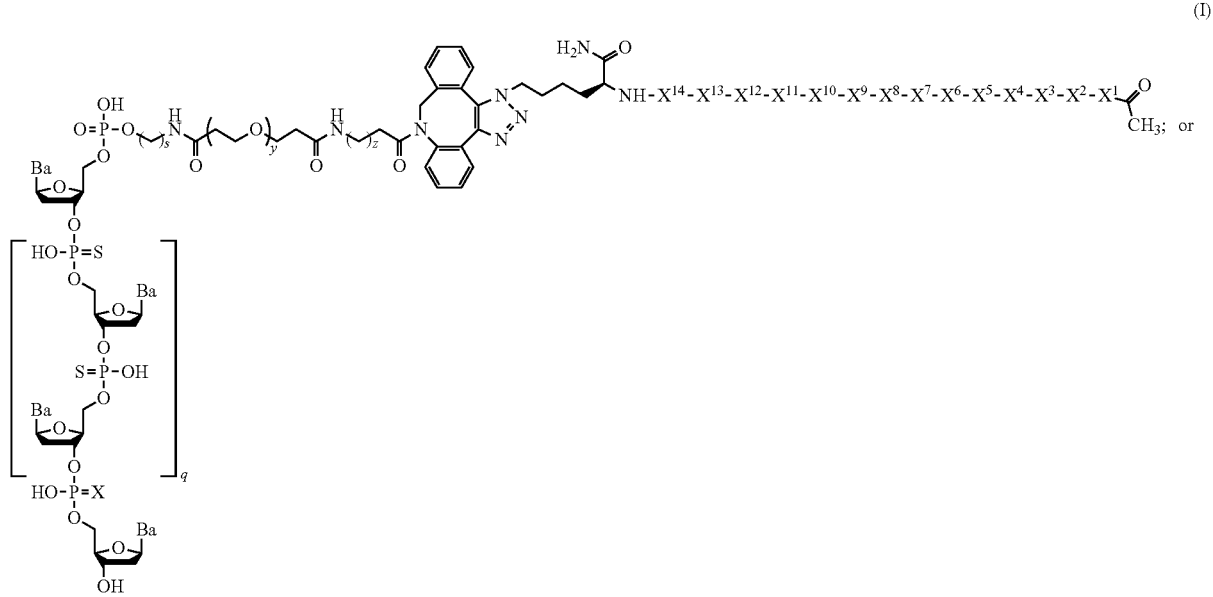

(I)

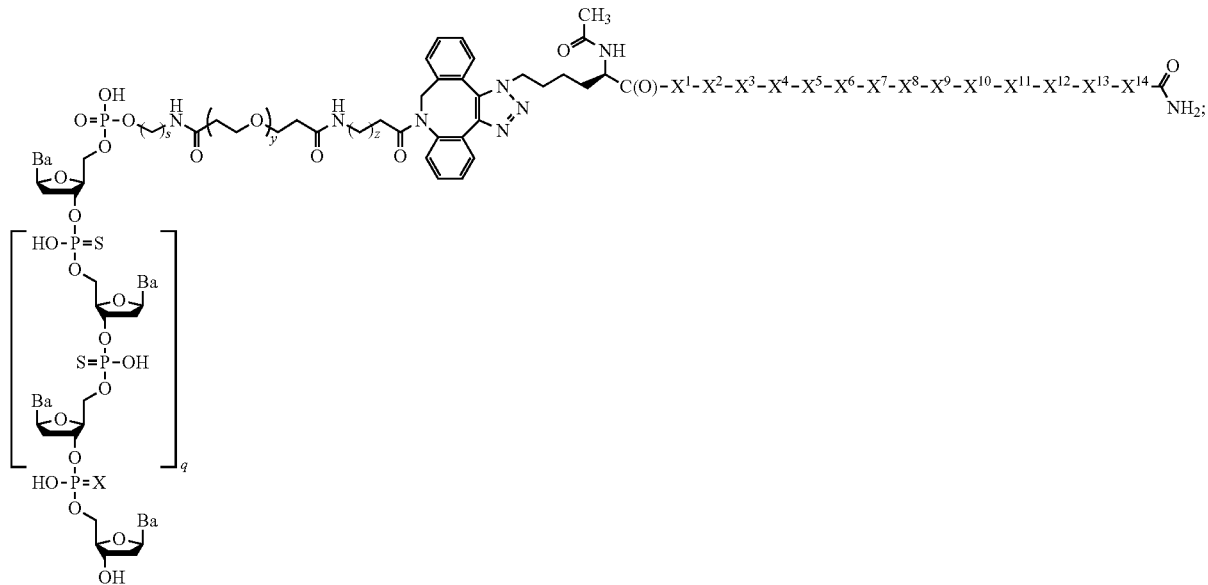

(II)

or a pharmaceutically acceptable salt thereof, wherein
each Ba is independently selected from adenine (A), guanine (G), cytosine (C), and thymine (T);
X is O or S;
q is an integer from 12 to 35;
s is an integer from 1 to 10;
y is an integer from 1 to 10;
z is an integer from 1 to 10;
each $X^1$ is independently selected from Leu, Val, and Ala;
each $X^2$ is independently selected from Thr and Ser;
each $X^3$ is Phe;
each $X^4$ is independently selected from Aib, Ala, and Glu;
each $X^5$ is independently selected from Glu, Asp, and His;
each $X^6$ is independently selected from Tyr, Phe, and Ser;
each $X^7$ is Trp;
each $X^8$ is independently selected from Aib, Ala, and Val;
each $X^9$ is independently selected from Gln and Asn;
each $X^{10}$ is Leu;
each $X^{11}$ is independently selected from Aib, Thr, and Ala;
each $X^{12}$ is independently selected from Ser and Thr;
each $X^{13}$ is independently selected from Ala and Gly; and
each $X^{14}$ is independently selected from Ala and Gly.

2. Definitions

The terms adenine (A), guanine (G), cytosine (C), and thymine (T) refer to the DNA nucleobases having the following structures:

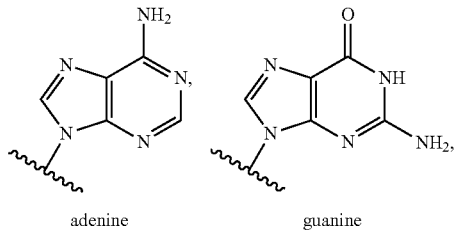

adenine  guanine

-continued

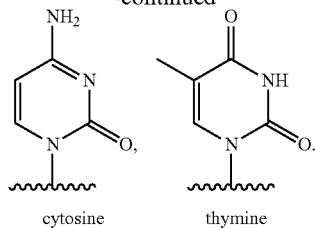

cytosine  thymine

The term "alkyl" used alone or as part of a larger moiety, such as "alkoxy", "haloalkyl", and the like, means saturated straight-chain or branched monovalent hydrocarbon radical. Unless otherwise specified, an alkyl group typically has 1-6 carbon atoms, i.e., $(C_1-C_6)$alkyl. As used herein, a "$(C_1-C_6)$ alkyl" group is means a radical having from 1 to 6 carbon atoms in a linear or branched arrangement.

The full name of a natural amino acid and its corresponding three-letter or one-letter code are used interchangeably. For example, glycine is interchangeable with three letter abbreviation Gly or the one letter abbreviation G; alanine is interchangeable with three letter abbreviation Ala or the one letter abbreviation A, valine is interchangeable with three letter abbreviation Val or the one letter abbreviation V, leucine is interchangeable with three letter abbreviation Leu or the one letter abbreviation L, isoleucine is interchangeable with three letter abbreviation Ile or the one letter abbreviation I, proline is interchangeable with three letter abbreviation Pro or the one letter abbreviation P, phenylalanine is interchangeable with three letter abbreviation Phe or the one letter abbreviation F, tyrosine is interchangeable with three letter abbreviation Tyr or the one letter abbreviation Y, tryptophan is interchangeable with three letter abbreviation Trp or the one letter abbreviation W, serine is interchangeable with three letter abbreviation Ser or the one letter abbreviation S, threonine is interchangeable with three letter abbreviation Thr or the one letter abbreviation T, cysteine is interchangeable with three letter abbreviation Cys or the one letter abbreviation C, methionine is interchangeable with three letter abbreviation Met or the one letter abbreviation M, asparagine is interchangeable with three letter abbreviation Asn or the one letter abbreviation N, glutamine is interchangeable with three letter abbreviation Gln or the one letter abbreviation Q, aspartate is interchangeable with three letter abbreviation Asp or the one letter abbreviation D, glutamate is interchangeable with three letter abbreviation Glu or the one letter abbreviation E, lysine is interchangeable with three letter abbreviation Lys or the one letter abbreviation K, arginine is interchangeable with three letter abbreviation Arg or the one letter abbreviation R, and histidine is interchangeable with three letter abbreviation His or the one letter abbreviation H.

The group "Aib" refers to the amino acid 2-amino isobutyric acid.

The peptide "Lys(N$_3$)" refers to an azido lysine of the structure

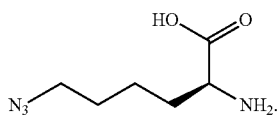 [SMILES: [N-]=[N+]=NCCCC[C@H](N)C(=O)O]

Acetyl or "Ac" refers to the group —COCH$_3$.

The disclosed compounds may exist in various stereoisomeric forms. Stereoisomers are compounds that differ only in their spatial arrangement. Diastereomers are stereoisomers that contain two or more asymmetrically substituted carbon atoms.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound, or mixtures enriched in one enantiomer relative to its corresponding optical isomer.

When a disclosed compound is named or depicted by structure without indicating the stereochemistry and e.g., the compound has more than one chiral center (e.g., at least two chiral centers), it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

Pharmaceutically acceptable salts of the compounds herein are contemplated. For use in medicines, the salts of the compounds described herein refer to non-toxic "pharmaceutically acceptable salts." Pharmaceutically acceptable salt forms include pharmaceutically acceptable acidic/anionic or basic/cationic salts.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" as used herein, refers to an amount of a compound disclosed herein, which is sufficient to effect treatment of a disease when administered to a subject. A therapeutically effective amount will vary depending upon the relative activity of the compound and depending upon the subject and disease condition being treated, the weight and age of the subject, the severity of the disease condition, the manner of administration and the like, which can readily be determined by one of ordinary skill in the art.

3. Description of Exemplary Compounds

In a first embodiment, the present disclosure provides a compound of Formula I or II:

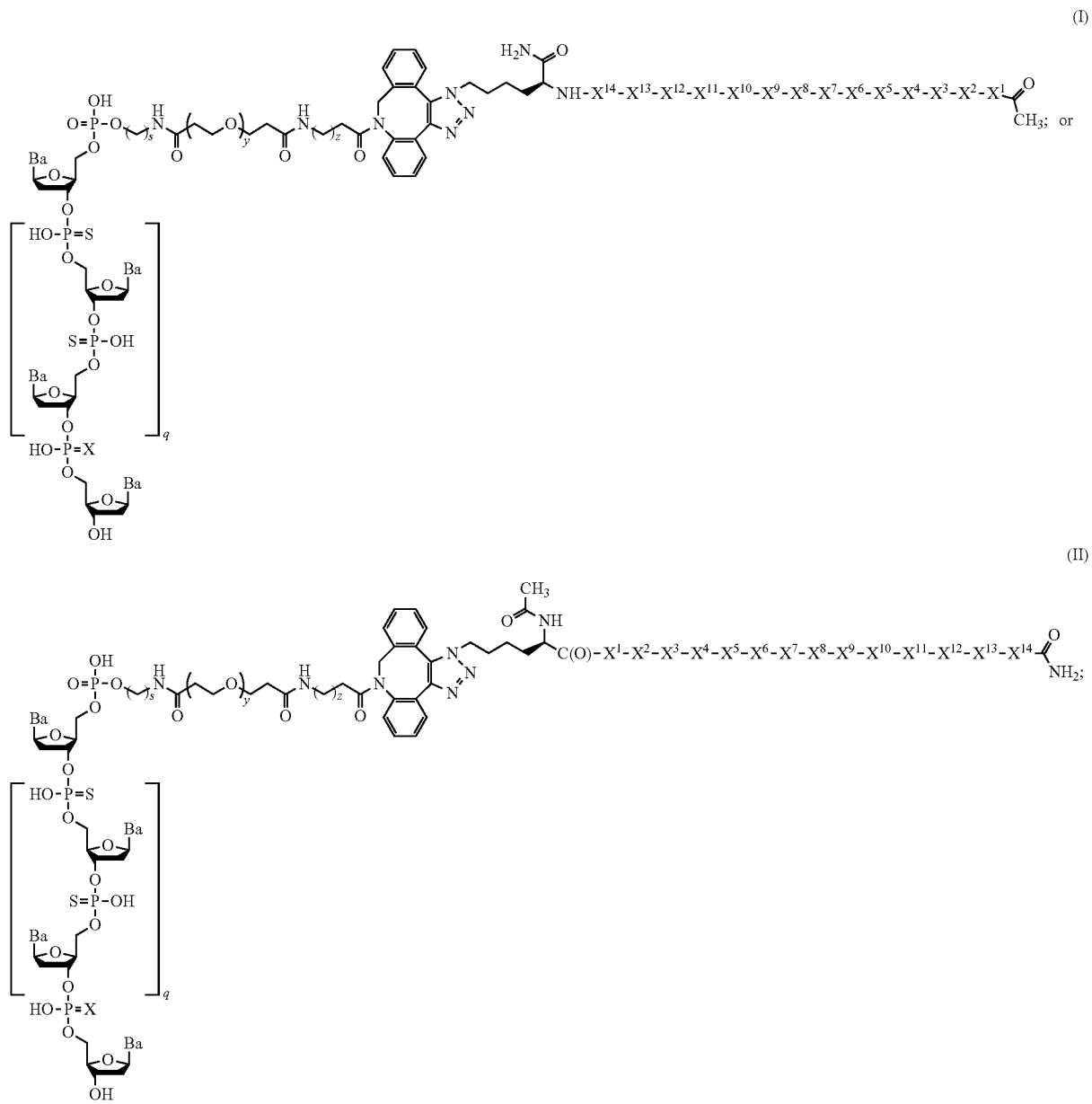

or a pharmaceutically acceptable salt thereof, wherein the variables are as described above.

In a second embodiment, X in the compound of Formula I or II is X is S, wherein the remaining variables are as described above for Formula I or II.

In a third embodiment, q in the compound of Formula I or II is an integer from 15 to 30, wherein the remaining variables are as described above for Formula I or II or the second embodiment. Alternatively, q in the compound of Formula I or II is an integer from 15 to 25, wherein the remaining variables are as described above for Formula I or II or the second embodiment. In another alternative, q in the compound of Formula I or II is 17, wherein the remaining variables are as described above for Formula I or II or the second embodiment.

In a fourth embodiment, s in the compound of Formula I or II is an integer from 1 to 8, wherein the remaining variables are as described above for Formula I or II or the second or third embodiment. Alternatively, s in the compound of Formula I or II is 6, wherein the remaining variables are as described above for Formula I or II or the second embodiment.

In a fifth embodiment, y in the compound of Formula I or II is an integer from 1 to 6, wherein the remaining variables are as described above for Formula I or II or the second, third, or fourth embodiment. Alternatively y in the compound of Formula I or II is 4, wherein the remaining variables are as described above for Formula I or II or the second, third, or fourth embodiment.

In a sixth embodiment, z in the compound of Formula I or II is an integer from 1 to 4, wherein the remaining variables are as described above for Formula I or II or the second, third, fourth, or fifth embodiment. Alternatively, z in the compound of Formula I or II is 1, wherein the remaining variables are as described above for Formula I or II or the second, third, fourth, or fifth embodiment.

In a seventh embodiment, the thiophosphate oligonucleotide sequence beginning at the 3' end in the compound of Formula I or II is TCCATGAGCTTCCTGATGCT (SEQ ID NO.: 1), wherein the remaining variables are as described above for Formula I or II or the second, third, fourth, fifth, or sixth embodiment.

Specific examples of compounds are provided in the EXEMPLIFICATION section. Pharmaceutically acceptable salts as well as the neutral forms of these compounds are included herein.

4. Uses, Formulation and Administration

In certain embodiments, the present disclosure provides a method of treating a patient (e.g., a human) with a disease or disorder defined herein comprising the step of administering to the patient an effective amount of a compound of Formula I or II, or a pharmaceutically acceptable salt or composition thereof.

The amount of a provided compound that may be combined with carrier materials to produce a composition in a single dosage form will vary depending upon the patient to be treated and the particular mode of administration.

Compounds or compositions described herein may be administered using any amount and any route of administration effective for treating or lessening the severity of one or more of the diseases and conditions described herein. A specific dosage and treatment regimen for any particular patient will depend upon a variety of factors, including age, body weight, general health, sex, diet, time of administration, rate of excretion, drug combination, the judgment of the treating physician, and the severity of the particular disease being treated.

Compounds and compositions described herein are useful for intracellular delivery of, or to enhance the intracellular delivery of, one or more antibodies. Thus, it will be appreciated that the present disclosure provides a method of treating a disease or disorder that could be treated by an inhibitor of the p-53/MDM2 interaction.

In certain embodiments, the compounds and compositions described herein are useful in treating cancer or other neoplastic condition in a subject in need thereof.

Exemplary types of cancer include e.g., adrenal cancer, acinic cell carcinoma, acoustic neuroma, acral lentiginous melanoma, acrospiroma, acute eosinophilic leukemia, acute erythroid leukemia, acute lymphoblastic leukemia (ALL), acute megakaryoblastic leukemia, acute monocytic leukemia, acute promyelocytic leukemia, acute myeloid leukemia (AML) adenocarcinoma, adenoid cystic carcinoma, adenoma, adenomatoid odontogenic tumor, adenosquamous carcinoma, megakaryocytic leukemia, adipose tissue neoplasm, chronic myeloid leukemia (CML), adrenocortical carcinoma, chronic myelomonocytic leukemia (CMML), adult T-cell leukemia/lymphoma, juvenile myelomonocytic leukemia (JMML), aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, large granular lymphocyte leukemia, angiomyolipoma, angiosarcoma, astrocytoma, atypical teratoid rhabdoid tumor, B-cell chronic lymphocytic leukemia (CLL), B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one aspect, the compounds described herein are useful for treating solid tumors, hematological cancers, liposarcoma, myelogenous leukemia, soft tissue sarcoma, acute myelogenous leukemia, prostate cancer, metastatic melanoma, polycythemia vera, and essential ihrombocythemia.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds described herein.

Conjugation Approach

Compound 100 was prepared using standard solid support procedures, i.e., the oligo was assembled on solid support followed by attachment of the C3-phosphoramidite spacer at 5' end one by one followed by dibenzocyclooctyltriethyleneglycolphosphoramidite ((DBCO)-TEG-phosphoramidite). The compound is then cleaved from solid support and purified via HPLC.

To 1.0 mL of compound 100 (concentration 3-8 mg/mL in PBS, pH 7.4) in an eppendurf tube was added 1.0 equivalent of peptide 200 in DMSO (50 μL). Variables are as described above and the peptide 200 was: Ac-Leu-Thr-Phe-Aib-Glu-Tyr-Trp-Aib-Gln-Leu-Aib-Ser-Ala-Ala-Lys($N_3$)—$NH_2$ (SEQ ID NO.: 2); Ac-Lys($N_3$)-Leu-Thr-Phe-Aib-Glu-Tyr-Trp-Aib-Gln-Leu-Aib-Ser-Ala-Ala-$NH_2$ (SEQ ID NO.: 3); or Ac-Leu-Thr-Phe-Glu-His-Tyr-Trp-Ala-Gln-Leu-Thr-Ser-Ala-Lys($N_3$)—$NH_2$ (SEQ ID NO.: 4). The tube was put on a rotating wheel and rotated at room temperature for 8-10 hours. See Scheme 1 below. The reaction was monitored by LCMS. After reaction, the mixture was purified by reverse phase HPLC.

Scheme 1:

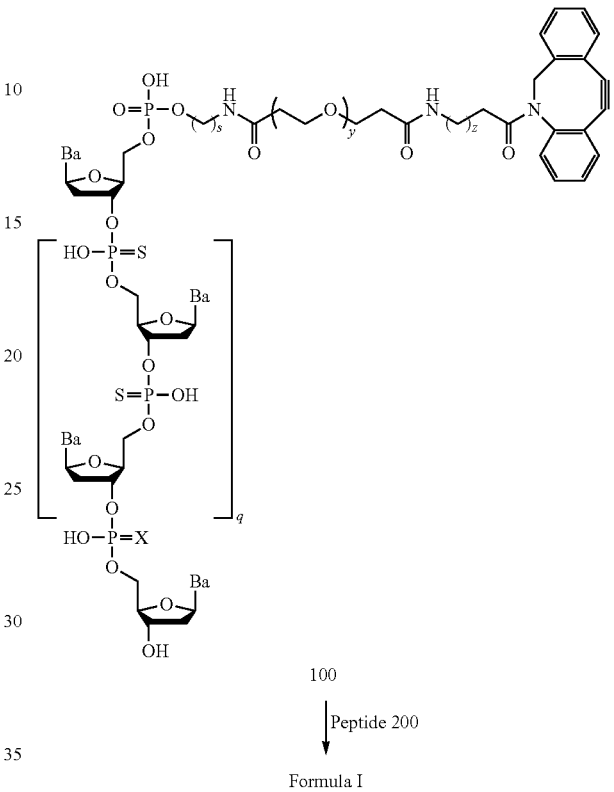

100

↓ Peptide 200

Formula I

Figure 2:
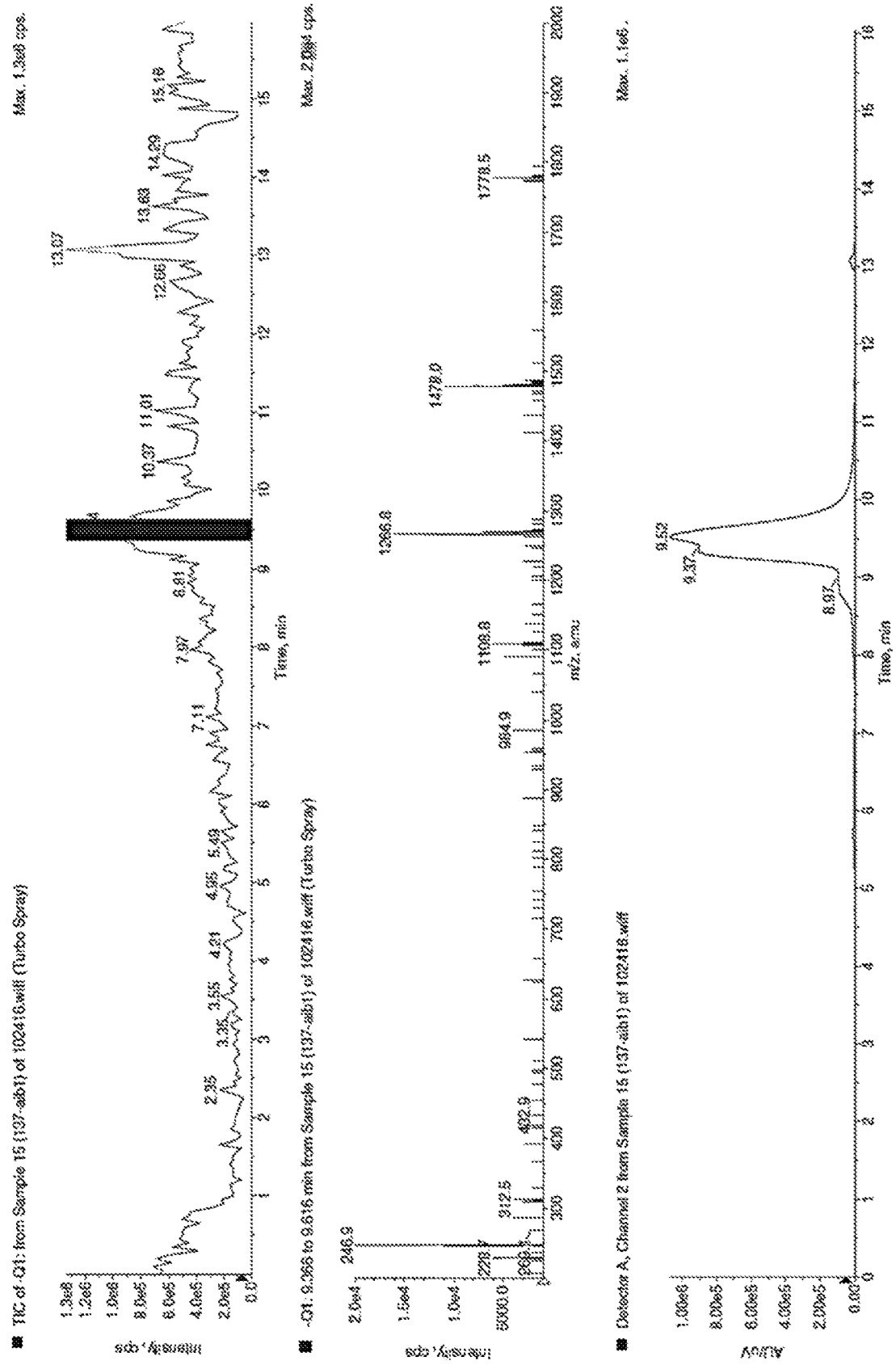
FIG. 2 is an LCMS spectrum of the crude reaction mixture for compound 110.
Figure 3:
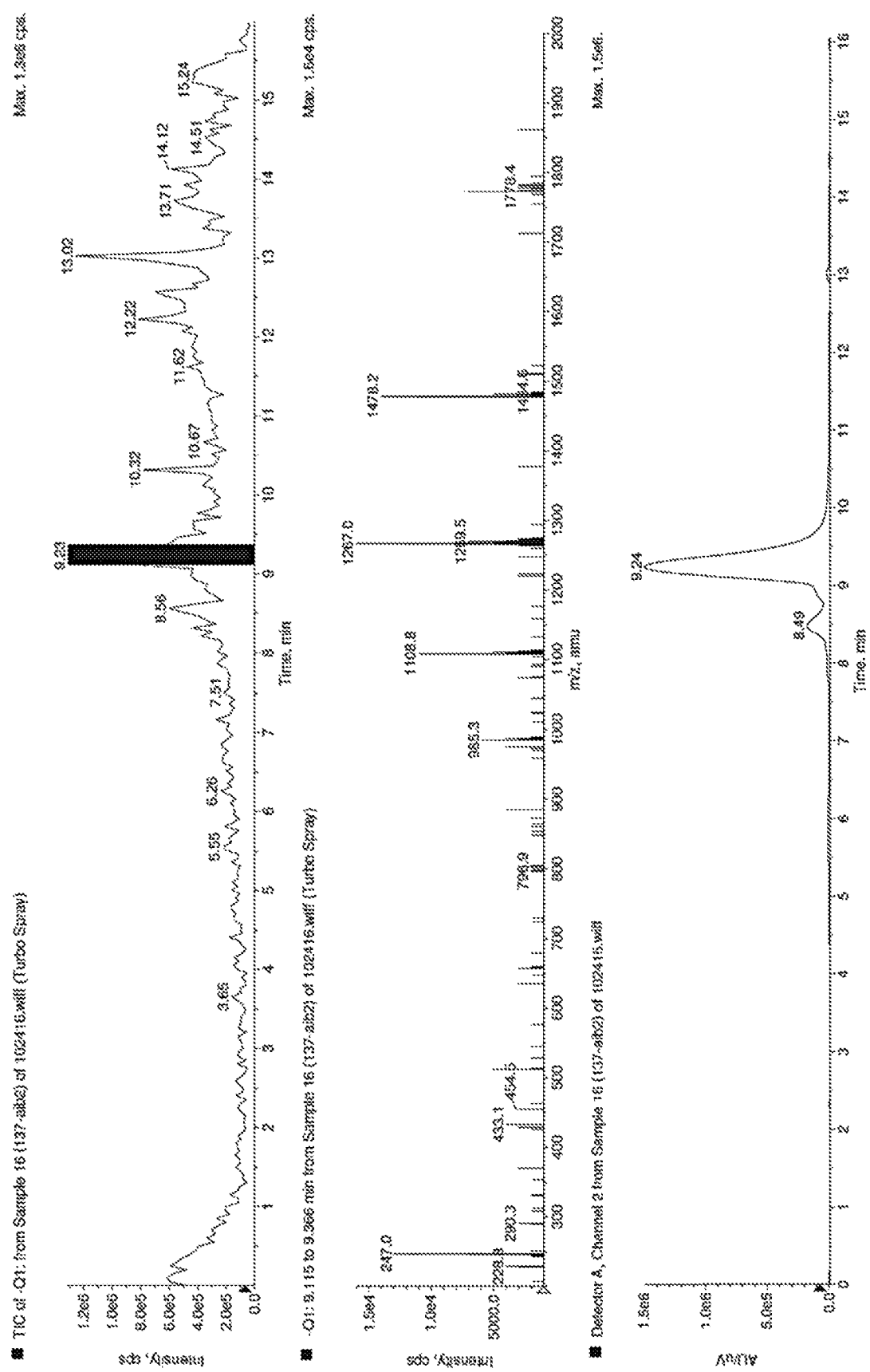
FIG. 3 is an LCMS spectrum of the crude reaction mixture for compound 120.
Figure 4:
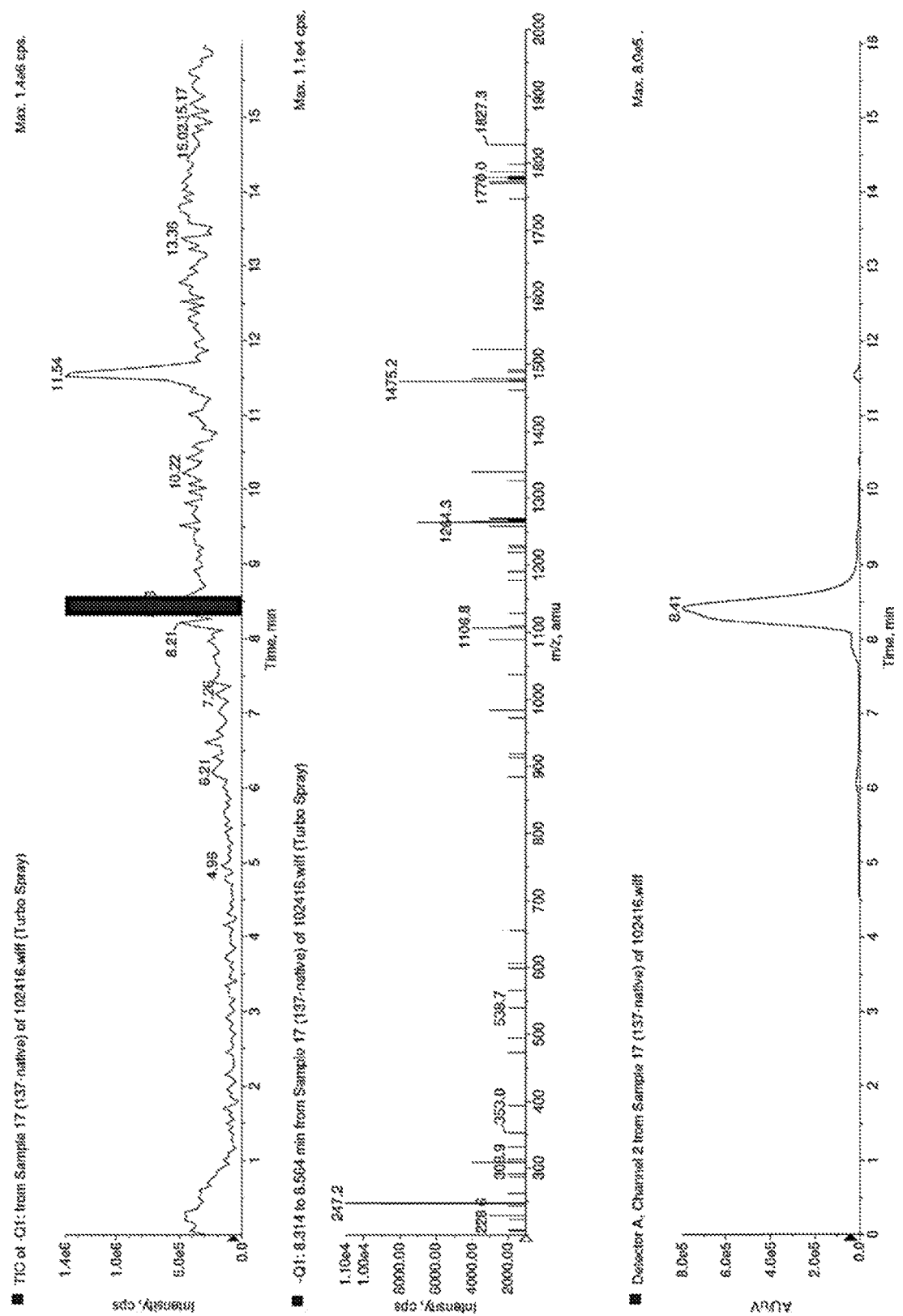
FIG. 4 is an LCMS spectrum of the crude reaction mixture for compound 130.

Following the procedures described above, the following products were generated. LCMS data for the crude reaction mixture containing these products are shown in FIGS. 2-4, respectively.

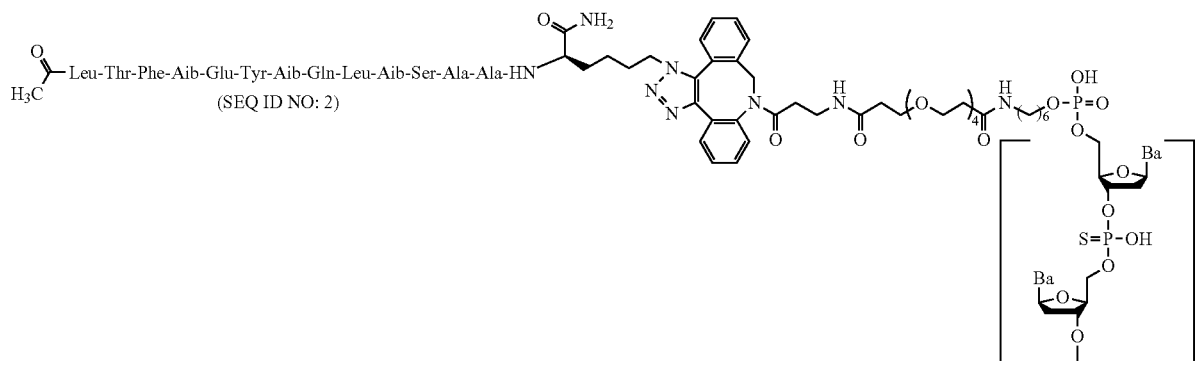

110

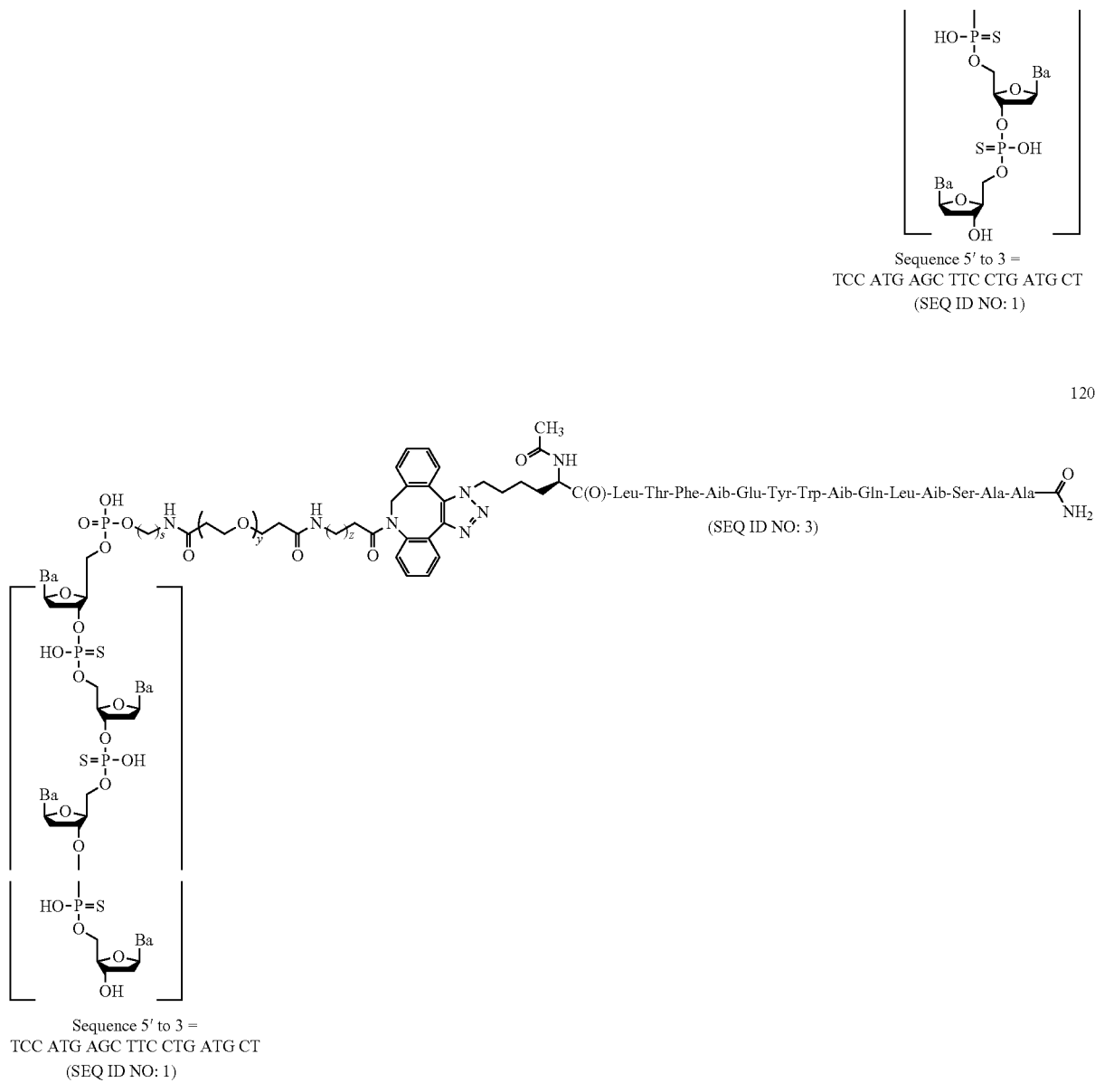
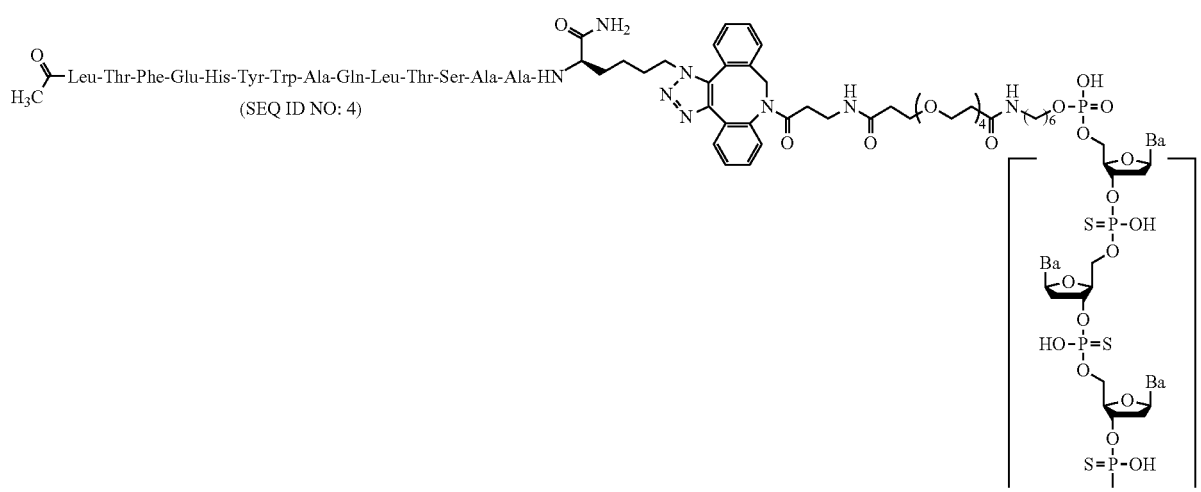

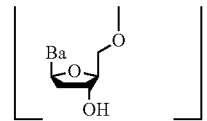

Sequence 5' to 3' =
TCC ATG AGC TTC CTG ATG CT
(SEQ ID NO: 1)

P53-MDM2 Inhibition

500K Hela cells were transfected with 2 ug p53 Halotag and MDM2-Nanoluc plasmids or MAX-Halotag and Myc-Nanoluc plasmids overnight with Attractene. Cells were reseeded in 96-well plate for 6 hours then treated with 110, 120, and 130 for 16 h. NanoBRET detection was added and dual-filtered luminescence was measured on Flexstation.

As shown by FIG. 1, compounds 110 and 120 inhibit p53/MDM2 interaction. In addition, compounds 110 and 120 did not significantly inhibit Myc/MAX interaction compared to scrambled and oligo only, suggesting specificity toward MDM2. Oligo refers to the oligo TCCATGAGCT-TCCTGATGCT (SEQ ID NO.: 1), which corresponds to the oligo sequence portion present in compounds 110, 120, and 130. PS-scrambled is the negative control and refers to a scrambled peptide with C-terminal conjugated to oligo (i.e., the peptide contains all of the amino acids in the tested examples, but with a scrambled sequence. Nutlin referes to the MDM2 inhibitor Nutlin-3.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:
1. A compound having the Formula I or II:
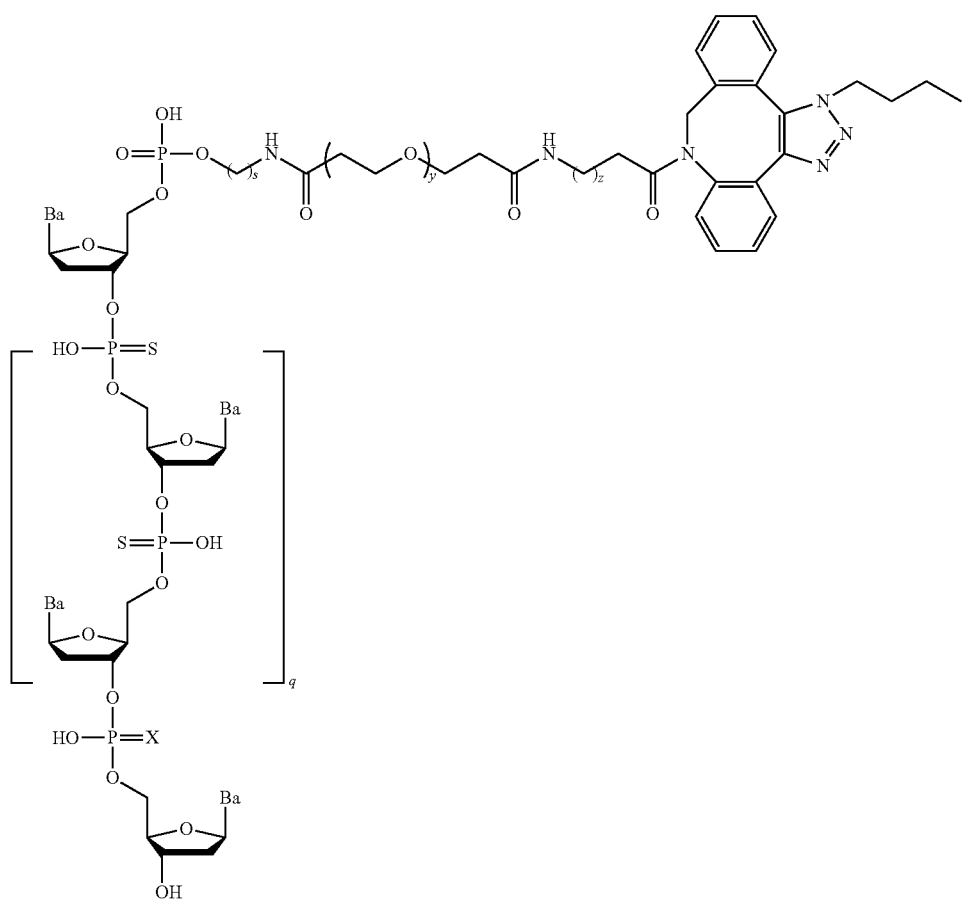
(I)
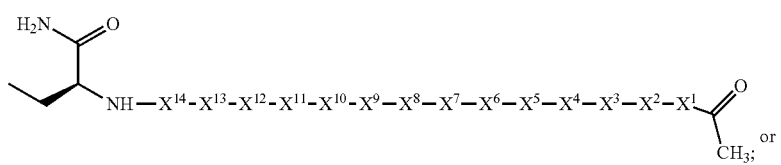
or

-continued (II)

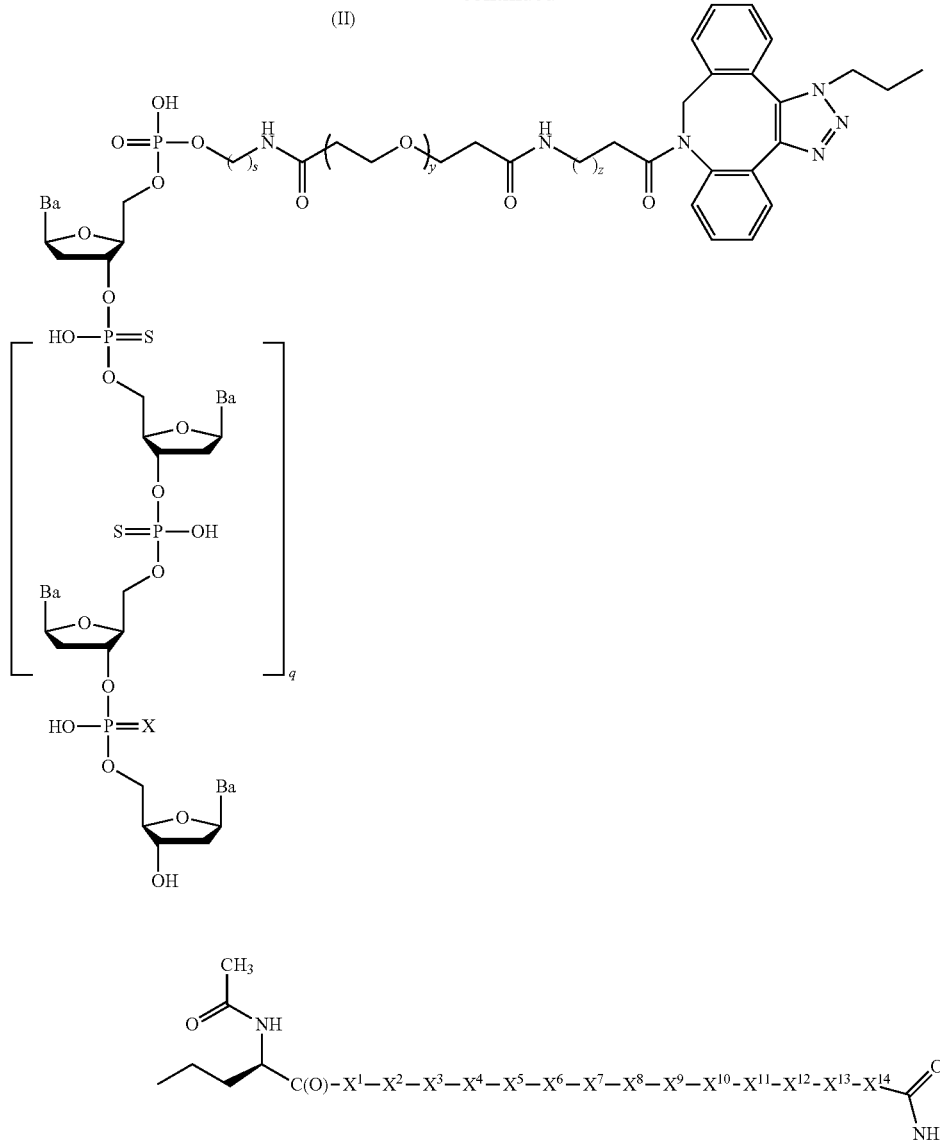

or a pharmaceutically acceptable salt thereof, wherein:
each Ba is independently selected from adenine (A), guanine (G), cytosine (C), and thymine (T);
X is O or S;
q is 9;
s is an integer from 1 to 10;
y is an integer from 1 to 10;
z is an integer from 1 to 10;
each $X^1$ is independently selected from Leu, Val, and Ala;
each $X^2$ is independently selected from Thr and Ser;
each $X^3$ is Phe;
each $X^4$ is independently selected from Aib, Ala, and Glu;
each $X^5$ is independently selected from Glu, Asp, and His;
each $X^6$ is independently selected from Tyr, Phe, and Ser;
each $X^7$ is Trp;
each $X^8$ is independently selected from Aib, Ala, and Val;
each $X^9$ is independently selected from Gln and Asn;
each $X^{10}$ is Leu;
each $X^{11}$ is independently selected from Aib, Thr, and Ala;
each $X^{12}$ is independently selected from Ser and Thr;
each $X^{13}$ is independently selected from Ala and Gly; and
each $X^{14}$ is independently selected from Ala and Gly.

2. The compound of claim 1, wherein X is S.

3. The compound of claim 1, wherein s is an integer from 1 to 8.

4. The compound of claim 1, wherein s is 6.

5. The compound of claim 1, wherein y is an integer from 1 to 6.

6. The compound of claim 1, wherein y is 4.

7. The compound of claim 1, wherein z is an integer from 1 to 4.

8. The compound of claim 1, wherein z is 1.

9. The compound of claim 1, wherein the thiophosphate oligonucleotide sequence is TCCATGAGCTTCCTGATGCT (SEQ ID NO.:1).

10. The compound of claim 1, wherein the compound is of the Formula:

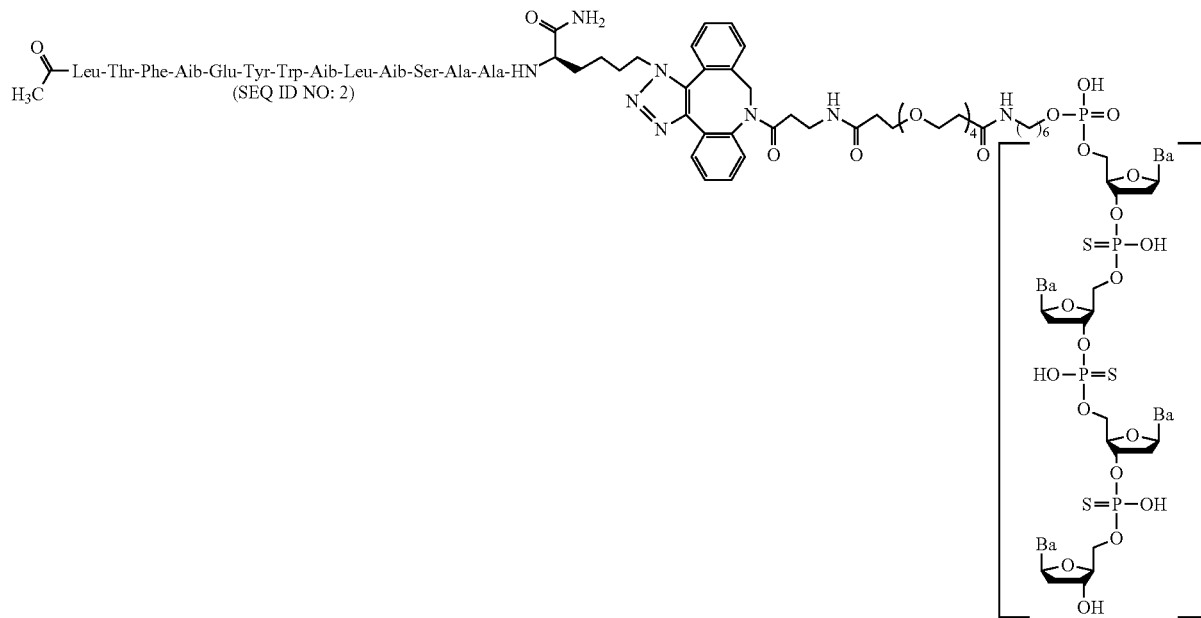
Sequence 5' to 3' =
TCC ATG AGC TTC CTG ATG CT
(SEQ ID NO: 1)
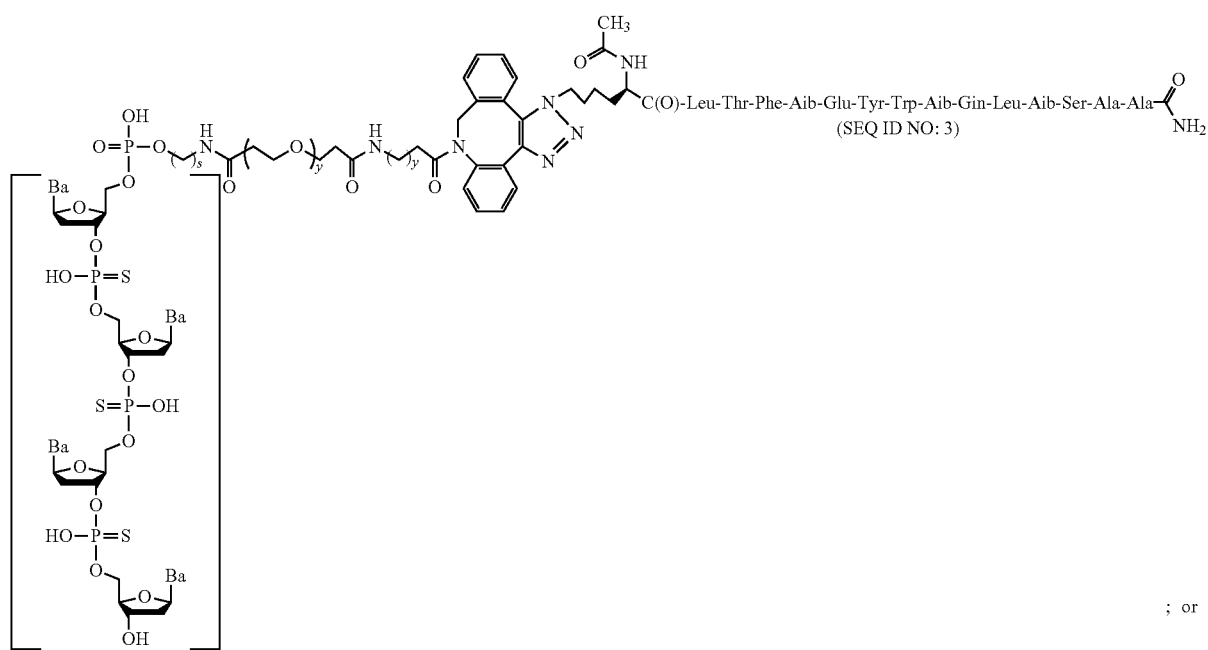
Sequence 5' to 3' =
TCC ATG AGC TTC CTG ATG CT
(SEQ ID NO: 1)

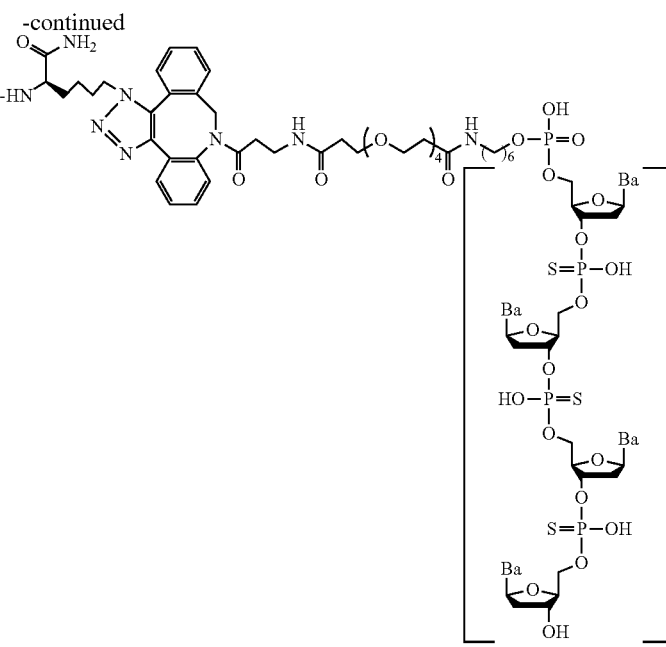

-continued

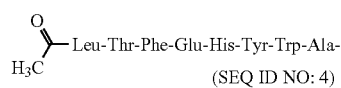-Leu-Thr-Phe-Glu-His-Tyr-Trp-Ala-Gin-Leu-Thr-Ser-Ala-Ala-HN (SEQ ID NO: 4)

Sequence 5' to 3' =
TCC ATG AGC TTC CTG ATG CT
(SEQ ID NO: 1)

or a pharmaceutically acceptable salt thereof.

11. A pharmaceutical composition comprising the compound of claim 1, or a pharmaceutically acceptable salt thereof; and a pharmaceutically acceptable carrier.

12. A method of delivering a peptide inhibitor of p53-MDM2 into a cell target comprising treating the cell with a compound of claim 1.

* * * * *